United States Patent
Guo et al.

(10) Patent No.: US 11,524,180 B2
(45) Date of Patent: Dec. 13, 2022

(54) MOUNTING MECHANISM AND RADIOTHERAPY DEVICE

(71) Applicant: SHENZHEN OUR NEW MEDICAL TECHNOLOGIES DEVELOPMENT CO., LTD., Shenzhen (CN)

(72) Inventors: Zhao Guo, Xi'an (CN); Ruirong Zhang, Xi'an (CN)

(73) Assignee: Shenzhen Our New Medical Technologies Development Co., Ltd., Shenzhen (CN)

( * ) Notice: Subject to any disclaimer, the term of this patent is extended or adjusted under 35 U.S.C. 154(b) by 44 days.

(21) Appl. No.: 17/288,881

(22) PCT Filed: Sep. 5, 2019

(86) PCT No.: PCT/CN2019/104498
§ 371 (c)(1),
(2) Date: Apr. 26, 2021

(87) PCT Pub. No.: WO2020/082906
PCT Pub. Date: Apr. 30, 2020

(65) Prior Publication Data
US 2021/0346724 A1   Nov. 11, 2021

(30) Foreign Application Priority Data

Oct. 26, 2018 (CN) .......................... 201811261454.9
Oct. 26, 2018 (CN) .......................... 201821758062.9

(51) Int. Cl.
*A61N 5/10* (2006.01)
(52) U.S. Cl.
CPC ................................. *A61N 5/1081* (2013.01)

(58) Field of Classification Search
CPC ...................................................... A61N 5/1081
See application file for complete search history.

(56) References Cited

U.S. PATENT DOCUMENTS

| 7,108,421 B2 * | 9/2006 | Gregerson | ........... | A61B 6/4021 |
| | | | | 378/146 |
| 2017/0065834 A1 * | 3/2017 | Liu | ....................... | A61N 5/1047 |

FOREIGN PATENT DOCUMENTS

| CN | 201625351 U | * | 11/2010 |
| CN | 203693622 U | | 7/2014 |
| CN | 204269574 U | | 4/2015 |
| CN | 104897702 A | * | 9/2015 |
| CN | 206434724 U | * | 8/2017 |
| CN | 107583208 A | * | 1/2018 |
| CN | 107583208 A | | 1/2018 |

(Continued)

OTHER PUBLICATIONS

International search report of PCT application No. PCT/CN2019/104498 dated Nov. 28, 2019.

*Primary Examiner* — Marcus H Taningco
(74) *Attorney, Agent, or Firm* — Knobbe, Martens, Olson & Bear, LLP

(57) ABSTRACT

A mounting mechanism includes: two lateral supports respectively connected to two sides of a radiation head; top supports connected to tops of the lateral supports and configured to be connected to a top of a gantry; and positioning supports connected to the gantry and disposed between the lateral supports and the gantry, wherein the thicknesses of the positioning supports are adjustable. A radiotherapy device is further provided.

20 Claims, 5 Drawing Sheets

(56) References Cited

FOREIGN PATENT DOCUMENTS

| | | | |
|---|---|---|---|
| CN | 207306675 U | | 5/2018 |
| CN | 111077564 A | * | 4/2020 |
| JP | H09131411 A | | 5/1997 |

* cited by examiner

MOUNTING MECHANISM AND RADIOTHERAPY DEVICE

CROSS-REFERENCE TO RELATED APPLICATIONS

This application is a US national phase application of international application No. PCT/CN2019/104498, filed on Sep. 5, 2019, which claims priority to Chinese Patent Application No. 201811261454.9, filed on Oct. 26, 2018 and entitled "MOUNTING MECHANISM AND RADIOTHERAPY EQUIPMENT," and Chinese Patent Application No. 201821758062.9, filed on Oct. 26, 2018 and entitled "MOUNTING MECHANISM AND RADIOTHERAPY EQUIPMENT," the contents of each of which are incorporated herein by reference in their entirety.

TECHNICAL FIELD

The present disclosure relates to the field of radiotherapy technologies, and in particular, relates to a mounting mechanism and a radiotherapy device.

BACKGROUND

Gamma knives and medical linear accelerators are common radiotherapy devices used for treatment of tumors. Typically, a gamma knife includes a gantry and a treatment head mounted on the gantry.

SUMMARY

The present disclosure provides a mounting mechanism and a radiotherapy device.

Specifically, the following technical solutions are provided.

According to an aspect, a mounting mechanism is provided. The mounting mechanism includes: two lateral supports respectively connected to two sides of a treatment head; top supports connected to the tops of the lateral supports and configured to be connected to a top of a gantry; and positioning supports connected to the gantry and disposed between the lateral supports and the gantry, wherein thicknesses of the positioning supports are adjustable.

In an optional embodiment, the positioning support includes a first fixing block connected to the gantry and a first thickness adjusting block slidable relative to the first fixing block.

The mounting mechanism further includes a first driving member configured to drive the first thickness adjusting block to bidirectionally slide.

In an optional embodiment, the first fixing block and the first thickness adjusting block are matched wedges.

In an optional embodiment, the first driving member and the first thickness adjusting block are in threaded connection.

In an optional embodiment, the mounting mechanism further includes: unloading supports, wherein the unloading supports are connected to the gantry and disposed between the lateral supports and the gantry, and thicknesses of the unloading supports are adjustable; and the unloading supports are provided with rolling members, wherein the rolling members are configured to form rolling friction with the lateral supports.

In an optional embodiment, the unloading support includes a second fixing block connected to the gantry and a second thickness adjusting block slidable relative to the second fixing block; and the mounting mechanism further includes a second driving member configured to drive the second thickness adjusting block to bidirectionally slide; wherein the rolling member is disposed on the second thickness adjusting block.

In an optional embodiment, the second fixing block and the second thickness adjusting block are matched wedges.

In an optional embodiment, the second driving member and the second thickness adjusting block are in threaded connection.

In an optional embodiment, the rolling member includes a fixed body fixed to the second thickness adjusting block and a plurality of balls rotatably disposed on the fixed body.

In an optional embodiment, the mounting mechanism further includes: top supports connected to the tops of the lateral supports; first positioning members disposed on the top supports; and second positioning members disposed at the top of the gantry; wherein the first positioning members and the second positioning members are in one-to-one correspondence.

According to another aspect, a radiotherapy device is provided. The radiotherapy device includes: any of the mounting mechanisms mentioned above; a treatment head, wherein the treatment head is connected to a lateral support of the mounting mechanism; and a gantry, wherein the gantry is connected to a positioning support of the mounting mechanism.

BRIEF DESCRIPTION OF THE DRAWINGS

For clearer descriptions of the technical solutions in the embodiments of the present disclosure the following briefly introduces the accompanying drawings required for describing the embodiments. Apparently, the accompanying drawings in the following description show merely some embodiments of the present disclosure, and a person of ordinary skill in the art may still derive other drawings from these accompanying drawings without creative efforts.

REFERENCE NUMERALS AND DENOTATIONS THEREOF

1—lateral support; 2—top support; 201—first positioning member; 202—second positioning member;
3—positioning support; 301—first fixing block; 302—first thickness adjusting block;
4—unloading support; 401—rolling member; 4011—fixed body; 4012—ball;
402—second fixing block; 403—second thickness adjusting block;

5—reinforcing support; 6—via hole; 7—first driving member; 8—second driving member; 9—reinforcing block; M—treatment head; N—gantry; P—mounting lateral plate.

DETAILED DESCRIPTION

For clearer descriptions of the technical solutions and advantages of the present disclosure, embodiments of the present disclosure are described in detail hereinafter with reference to the accompanying drawings.

It should be noted that a treatment head of a radiotherapy device includes but is not limited to a therapy head and an imaging head. The treatment head is mounted on a gantry which is correspondingly provided with a mounting position to accommodate the treatment head. Generally, there are two mounting lateral plates at the mounting position of the gantry, wherein the lateral plates are configured to be connected to two sides of the treatment head (usually guide rails on two sides). It should be understood that the corresponding treatment heads have different names according to the specific radiotherapy devices. For example, a treatment head of a gamma knife is called a focused treatment head, and a treatment head of a linear accelerator is called an accelerator treatment head.

Currently, fitting spacers are usually disposed between guide rails on two sides of the treatment head and mounting lateral plates of the gantry on the same sides, and the position of the treatment head on the gantry is adjusted by selecting the fitting spacers with different thicknesses, so as to achieve a favorable mounting accuracy and rigidity.

However, this process requires repeated mounting and dismounting of the heavy treatment head, which increases the mounting difficulty.

According to an embodiment of the present disclosure, a mounting mechanism that is beneficial to mounting of a treatment head is provided based on the above structures of the treatment head and the gantry. The structure of the mounting mechanism is briefly described hereinafter.

Figure 1:
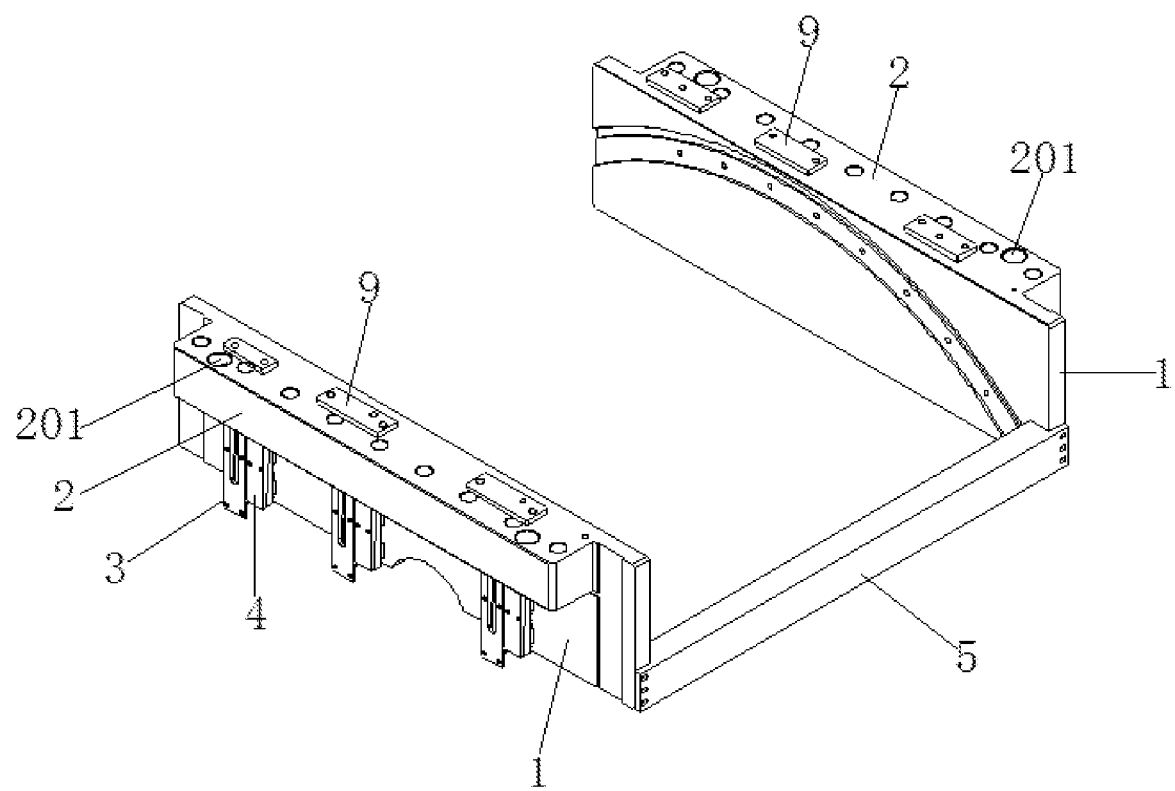
FIG. 1 is a schematic structural diagram of a mounting mechanism according to an embodiment of the present disclosure, in which a positioning support and an unloading support are attached to but not mounted on a lateral support.
Figure 2:
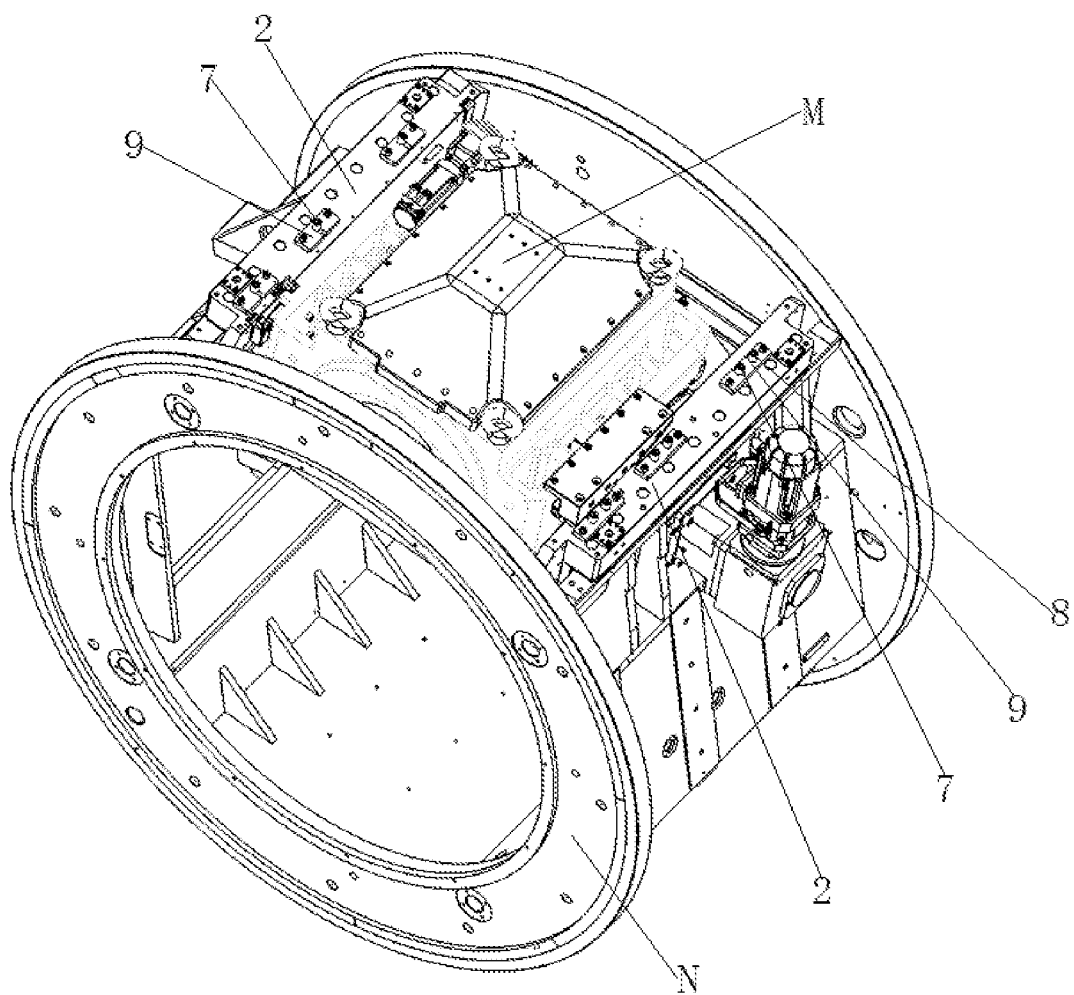
FIG. 2 is a schematic structural diagram of a radiotherapy device according to an embodiment of the present disclosure.
Figure 3:
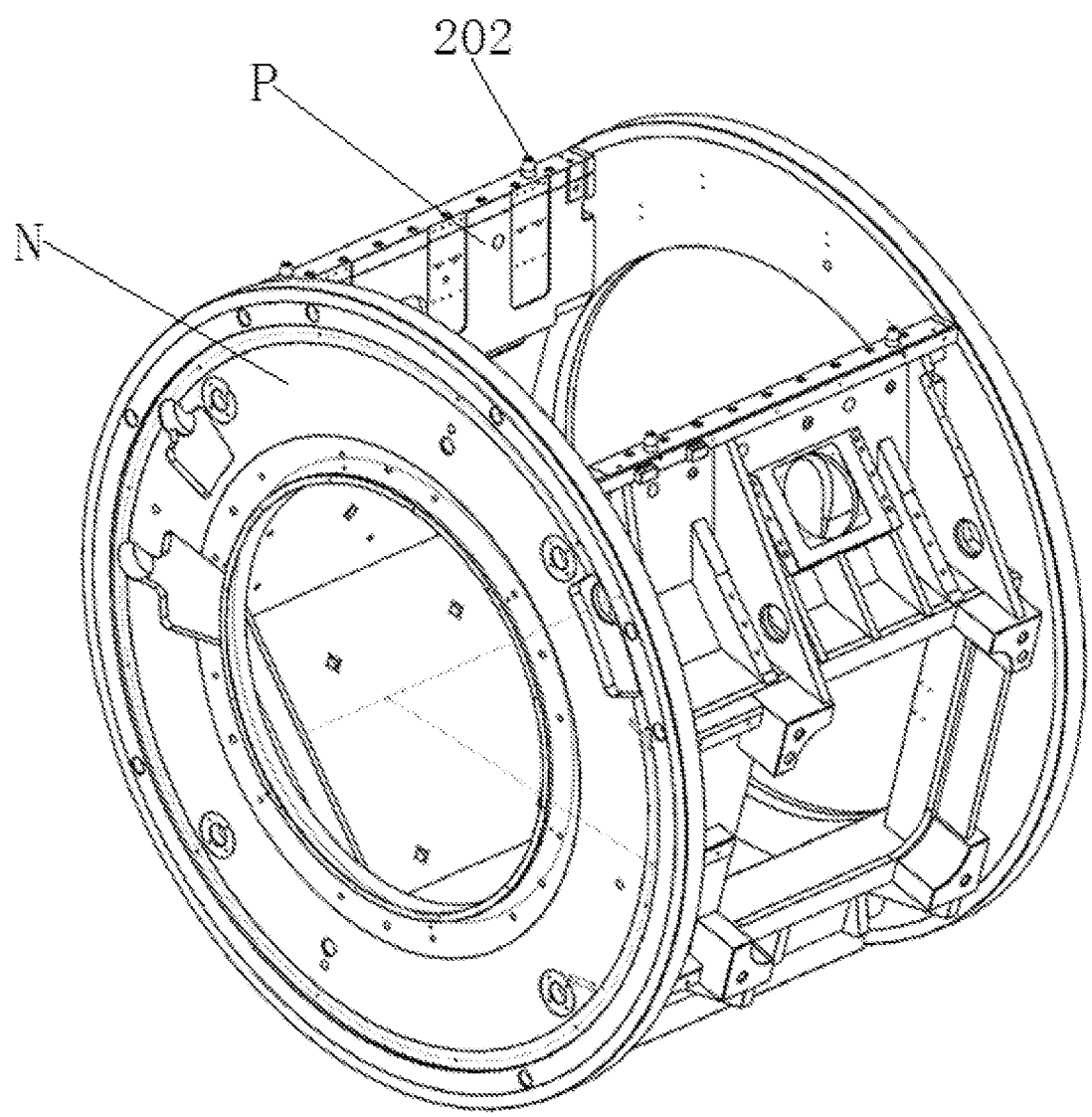
FIG. 3 is a schematic structural diagram of a gantry.

According to an aspect of the embodiments of the present disclosure, a mounting mechanism is provided. The mounting mechanism may be configured to mount and dismount a treatment head M of a radiotherapy device. As shown in FIGS. 1 to 3, the mounting mechanism includes two lateral supports 1 respectively connected to two sides of a treatment head M, top supports 2 connected to tops of the lateral supports 1 and configured to be connected to a top of a gantry N, and positioning supports 3 connected to the gantry N and disposed between the lateral supports 1 and the gantry N, wherein thicknesses of the positioning supports 3 are adjustable.

In application of the mounting mechanism provided by this embodiment, the top support 2 is connected to the top of the gantry N to preliminarily mount the treatment head M on the gantry N. The positioning support 3 connected to the gantry N is disposed between the lateral support 1 and the gantry N. By adjusting the thickness of the positioning support 3 until a mounting gap between the lateral support 1 and the gantry N is eliminated, i.e., the lateral support 1 and the positioning support 3 are closely attached to each other, the positioning support 3 may provide lateral support for the treatment head M, which effectively improves the mounting rigidity of the treatment head M and ensures a high mounting accuracy of the treatment head M. Then, the treatment head M may be subsequently connected and fastened to the gantry N. It can be seen that in the mounting process on the basis of the mounting mechanism according to this embodiment, a good mounting rigidity can be obtained and a high mounting accuracy can be ensured, and the treatment head M does not need to be repeatedly mounted and dismounted in the mounting process, which remarkably simplifies the mounting process and reduces the mounting difficulty.

In this embodiment, the positioning support 3 can effectively improve the mounting rigidity of the treatment head M, and provide stable lateral support for the treatment head M in use. For thickness adjustability of the positioning support 3, the applicable structure is briefly described hereinafter.

Figure 4:
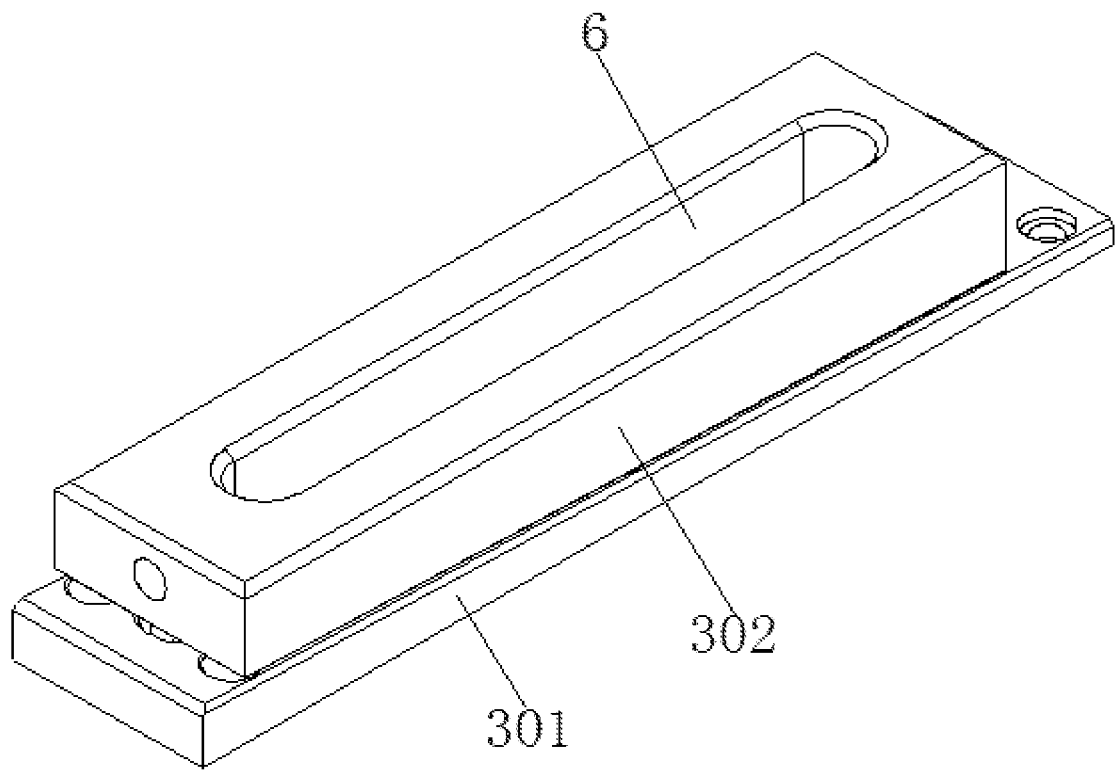
FIG. 4 is a schematic structural diagram of a positioning support according to an embodiment of the present disclosure.

In an example embodiment, as shown in FIG. 4, the positioning support 3 includes a first fixing block 301 connected to the gantry N (e.g., a mounting lateral plate p of the gantry N in FIG. 3), and a first thickness adjusting block 302 slidable relative to the first fixing block 301. Furthermore, as shown in FIG. 2, the mounting mechanism further includes a first driving member 7 configured to drive the first thickness adjusting block 302 to bidirectionally slide.

In practice, the first fixing block 301 may be fixedly connected to the mounting lateral plate P of the gantry N, and the first thickness adjusting block 302 and the first fixing block 301 form a sliding pair. The first driving member 7 can be used to drive the first thickness adjusting block 302 to bidirectionally slide along the first fixing block 301, such that the thickness of the positioning support 3 may be increased or reduced. Thus, the mounting gap between the lateral support 1 and the mounting lateral plate P of the gantry N can be eliminated or regained.

As for the sliding of the first thickness adjusting block 302 relative to the first fixing block 301, a sliding groove and a sliding rail may be disposed on their contact surfaces. For example, a sliding rail may be disposed on the first thickness adjusting block 302 and a sliding groove may be disposed on the first fixing block 301, such that the relative sliding may be achieved by cooperation between the sliding rail and the sliding groove. It should be understood that the sliding groove is longer than the sliding rail, such that the first thickness adjusting block 302 may bidirectionally slide along the first fixing block 301.

Figure 5:
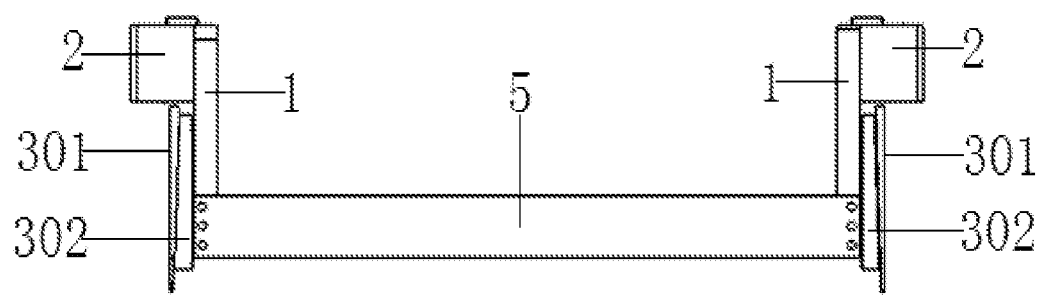
FIG. 5 is a schematic diagram of an operating relationship between a positioning support and a lateral support according to an embodiment of the present disclosure.

Considering that the first fixing block 301 is closely attached to the mounting lateral plate P of the gantry N, and the first thickness adjusting block 302 needs to be closely attached to the lateral support 1 (see FIG. 5), when the lateral support 1 is in a flat-plate-shaped structure, it is expected that the surface of the first thickness adjusting block 302 to which the lateral support is attached is also a plane. In view of this, for the purpose of thickness variation and for ensuring that the first fixing block 301 and the first thickness adjusting block are always closely attached to each other when the first thickness adjusting block 302 is bidirectionally sliding along the first fixing block 301, in this embodiment, as shown in FIG. 4, the first fixing block 301 and the first thickness adjusting block 302 are matched wedges, such that the first thickness adjusting block 302 may be tightly wedged to the lateral support 1 to form lateral support.

For example, the first fixing block 301 may be a wedge with a rectangular profile, and its thickness may gradually decrease from top to bottom; and the first thickness adjusting block 302 may also be a wedge with a rectangular profile, and its thickness may gradually increase from top to bottom. That is, fitting surfaces of the first fixing block 301 and the first thickness adjusting block 302 are matched inclined surfaces.

As mentioned above, the first driving member 7 is configured to drive the first thickness adjusting block 302 to bidirectionally slide. As an example, the first driving member 7 and the first thickness adjusting block 302 may be in threaded connection, and thus by rotating the first driving member 7 in situ and changing a rotating direction, the first thickness adjusting block 302 may bidirectionally slide.

The first driving member 7 may be limited on the top support 2 to ensure the in-situ rotation. In an example embodiment, the first driving member 7 may be a bolt, which may run through the top support 2 and be in threaded connection to the first thickness adjusting block 302. Moreover, the first driving member may be always limited on the top support based on the limiting function of its head, so as to achieve the purpose of being rotatable but not axially movable. At the same time, when the first driving member is a bolt, the first thickness adjusting block 302 and the lateral support 1 can be kept in a wedged state all the time, thereby ensuring that the lateral support 1 and the mounting lateral plate P of the gantry N are always in a wedged state.

Further, a reinforcing block 9 may be disposed on the top support 2, such that the first driving member 7 may simultaneously run through the reinforcing block 9 and the top support 2 to be in threaded connection with the first thickness adjusting block 302. Thus, the strength at the joints may be improved. The reinforcing block 9 may be in a plate-shaped structure.

Further, the mounting mechanism according to this embodiment may further include an unloading support 4 connected to the gantry N and disposed between the lateral support 1 and the gantry N. The unloading support 4 is provided with a rolling member 401, wherein the rolling member 401 is configured to form rolling friction with the lateral support 1. The unloading support 4 is adjustable in thickness.

The unloading support 4 and the positioning support 3 may cooperate to dismount and re-mount the treatment head M. In an example embodiment, when the treatment head M is to be dismounted, the gantry N is rotated to dispose the treatment head M on one side of the gantry N (i.e., a central axis of the treatment head M extends in a horizontal direction). The preliminary mounting of the top support 2 at the top of the gantry N is relieved, and the thickness of the positioning support 3 is adjusted until the mounting gap between the lateral support 1 and the gantry N is regained, i.e., the positioning support 3 is separated from the lateral support 1 for the convenience of dismounting. Then, the thickness of the unloading support 4 is adjusted to eliminate the gap between the lateral support 1 and the gantry N, and the unloading support 4 is configured to provide lateral support for the treatment head M, such that the treatment head M may be favorably positioned relative to the gantry N (this process can be understood as switching the positioning support 3 to the unloading support 4). Since the unloading support 4 is provided with the rolling member 401, which is configured to form rolling friction with the lateral support 1, based on the rolling friction, the treatment head M may be successfully pulled out of the gantry N by a treatment head dismounting tool (it should be understood that the treatment head M may be pulled out of the gantry N together with the lateral support 1 and the top support 2 of the mounting mechanism) after the fastening connection between the treatment head M and the gantry N is relieved. During re-mounting of the treatment head M, the mounting accuracy of the remounted treatment head M may be ensured only by returning along the original way and switching the unloading support 4 to the lateral support 1.

It can be seen that a mounting state of the treatment head M (i.e., the positioning support 3 acts) may be switched to a dismounting state (i.e., the unloading support 4 acts) by switching the positioning support 3 and the unloading support 4, and by the switching, the treatment head M may always maintain a favorable mounting accuracy when re-mounting after dismounted. Thus, on the premise of keeping the mounting accuracy, the treatment head M may be dismounted from the gantry N, and thus the treatment head M can be operated as needed, such as component maintenance or source replacement, more conveniently and feasibly, which is of great significance for reducing the size and the cost of the radiotherapy device and effectively improving the product competitiveness.

The lateral support 1 may be configured to be connected to guide rails on two sides of the treatment head M. According to the shapes of the guide rails, connecting positions matching with the shapes of the guide rails may be disposed on the lateral supports 1. Generally, the guide rails on the two sides of the treatment head M are semi-circular arc. At this time, semi-circular arc-shaped connecting groove may be disposed on the lateral support 1 as the connecting positions. After the guide rails are clamped into the connecting positions for preliminary positioning, the only requirement is to connect and fasten the guide rails to the connecting positions by fasteners (e.g., screws).

Both the positioning support 3 and the unloading support 4 may be connected to the mounting lateral plate P of the gantry N. At this time, the lateral support 1 is disposed between the guide rail of the treatment head M and the mounting lateral plate P of the gantry N. For close attachment of the lateral support 1 to the mounting lateral plate P of the gantry N, the lateral support 1 may be in a plate-shaped structure. Similarly, the top support 2 may also be in a plate-shaped structure. For improving the strength of the mounting mechanism, the lateral support 1 and the top support 2 may be integrally formed.

The unloading support 4 may be disposed on one or both of the two mounting lateral plates P of the gantry N at the same time. In view of that a favorable unloading effect may be achieved when the unloading support is only disposed on one side, in this embodiment, the unloading support 4 may only be disposed on the mounting lateral plate P on one side of the gantry N.

As mentioned above, the unloading support 4 is configured to laterally support the treatment head M in the process of dismounting the treatment head M. For thickness adjustability of the unloading support 4, its applicable structure is briefly described hereinafter.

Figure 6:
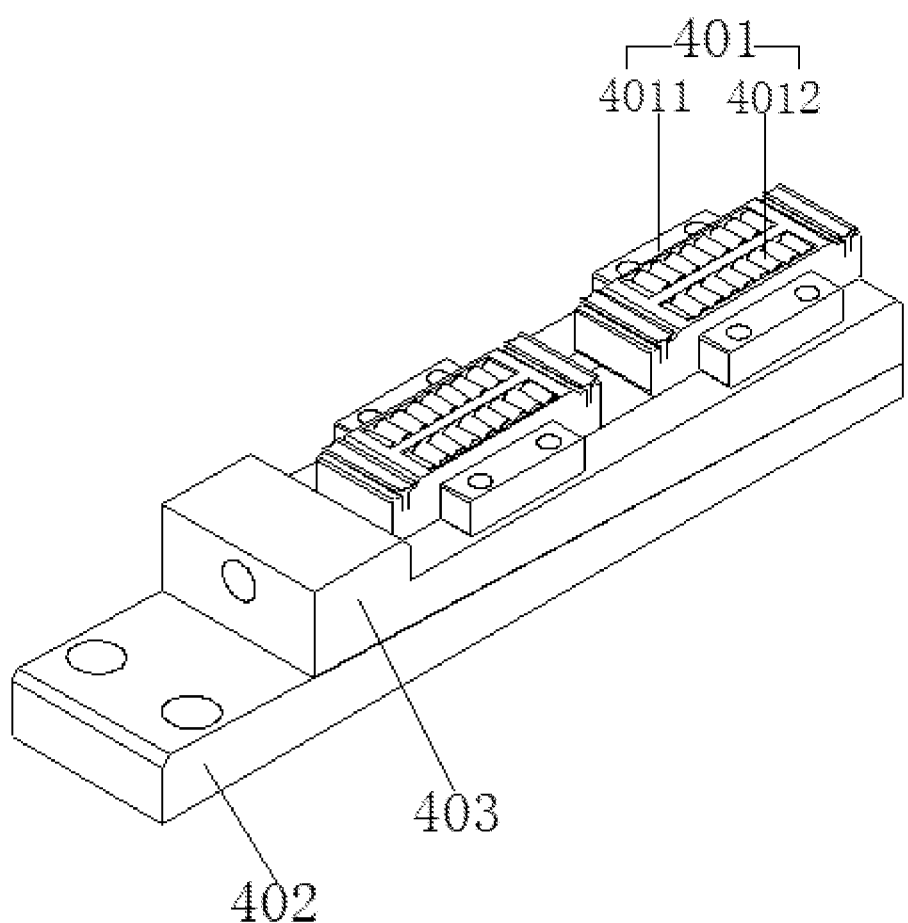
FIG. 6 is a schematic structural diagram of an unloading support according to an embodiment of the present disclosure.

In an example embodiment, as shown in FIG. 6, the unloading support 4 includes a second fixing block 402 connected to the gantry N (e.g., the mounting lateral plate P of the gantry in FIG. 3), and a second thickness adjusting block 403 slidable relative to the second fixing block 402. The rolling member 401 is disposed on the second thickness adjusting block 403.

Further, the mounting mechanism further includes a second driving member 8 configured to drive the second thickness adjusting block 403 to bidirectionally slide.

In practice, the second fixing block 402 may be fixedly connected to the mounting lateral plate P of the gantry N, and the second thickness adjusting block 403 and the second fixing block 402 form a sliding pair. The second driving member 8 may be used to drive the second thickness adjusting block 403 to bidirectionally slide along the second fixing block 402, such that the thickness of the unloading support 4 may be increased or reduced. Thus, the mounting gap between the lateral support 1 and the mounting lateral plate P of the gantry N can be eliminated or regained.

Reference may be made to the descriptions about the first thickness adjusting block 302 and the first fixing block 301 for the relative sliding manner of the second thickness adjusting block 403 to the second fixing block 402, which is not described repeatedly herein. In addition, the second fixing block 402 and the second thickness adjusting block 403 may also be matched wedges.

The second driving member 8 is in threaded connection to the second thickness adjusting block 403, so as to cause the second thickness adjusting block 403 bidirectionally slide. In an example embodiment, the second driving member 8 may also be a bolt.

Similarly, the second driving member 8 may also simultaneously run through the reinforcing block 9 and the top support 2 and be in threaded connection to the second thickness adjusting block 403. Thus, the strength at the joints may be improved. In this way, the unloading support 4 may be adjacently arranged to the positioning support 3 on the same side.

In this embodiment, the rolling member 401 is configured to form rolling friction with the lateral support 1. As an example, the rolling member 401 includes a fixed body 4011 secured onto the second thickness adjusting block 403 and a plurality of balls 4012 rotatably disposed on the fixed body 4011. The rolling friction may be formed between the balls 4012 and the lateral support 1. It should be understood that reference may be made to the structure of an abacus for the structure of the rolling member 401, which is not described in detail herein.

For optimization of the functions of the positioning support 3 and the unloading support 4, a plurality of positioning supports 3 and unloading supports 4 may be provided at the same time. In some embodiments, a plurality of positioning supports 3, e.g., 2, 3 (see FIG. 1) or 4, may be provided on the mounting lateral plate P on each side of the gantry N. Meanwhile, a plurality of unloading supports 4, e.g., 2, 3 (see FIG. 1) or 4, may be provided on the mounting lateral plate P on either side of the gantry N.

In order to quickly and effectively improve the mounting accuracy of the treatment head M, the mounting mechanism further includes a top support 2 connected to the top of the lateral support 1, a first positioning member 201 disposed on the top support 2, and a second positioning member 202 disposed on a top of the gantry N. The first positioning members 201 and the second positioning members 202 are in one-to-one correspondence.

During the preliminary mounting process of the treatment head M on the gantry N, the first positioning members 201 on the top support 2 one-to-one correspond to the second positioning members 202, and the first positioning members and the second positioning members cooperate to position the treatment head on the gantry, such that the mounting accuracy may be improved. After the positioning is achieved, the top support 2 is connected to the gantry N to secure the treatment head to the gantry. Based on the first positioning member 201 and the second positioning member 202, a high mounting accuracy can be achieved when the treatment head M is preliminarily mounted on the gantry N, and then the mounting rigidity of the treatment head M may be adjusted by the positioning support 3. In this way, repeated mounting and dismounting of the heavy treatment head are avoided on the premise of quickly and efficiently achieving a high mounting accuracy and a mounting rigidity, which remarkably simplifies the mounting process and reduces the mounting difficulty.

The gantry N may support the top support 2, and there may be more than one first positioning member 201 on the same top support 2, e.g., 2 or 3. It should be understood that the number of second positioning members 202 equals the number of first positioning members 201.

As mentioned above, the first positioning members 201 and the second positioning members 202 correspond to each other, thereby achieving positioning of the treatment head in the mounting process, and the first positioning members 201 and the second positioning members 202 may be connected to achieve connection between the top support 2 and the top of the gantry N. The positioning connection modes between the first positioning members 201 and the second positioning members 202 include but are not limited to plug connection, bolt connection, welded connection, snap connection, and the like, and for fast and effective connection, plug connection may be selected. The above connection modes are respectively described below.

For the bolt connection, both the first positioning members 201 and the second positioning members 202 may be bolt holes. In practice, the first positioning members 201 and the second positioning members 202 are communicated in one-to-one correspondence, and the two positioning members are connected by a bolt in threaded connection, so as to achieve effective positioning, and at the same time, the top support 2 can be connected to the top of the gantry N.

For the welded connection, both the first positioning members 201 and the second positioning members 202 may be indicators. In practice, the first positioning members 201 and the second positioning members 202 are overlapped in one-to-one correspondence, and then the top support 2 is welded to the top of the gantry, so as to achieve effective positioning and to achieve connection between the top support 2 and the top of the gantry N at the same time.

For the snap connection, the first positioning members 201 may be clamping grooves and the second positioning members 202 may be clamps. In practice, the second positioning members 202 may be clamped into the first positioning members 201, so as to achieve effective positioning and to achieve connection between the top support 2 and the top of the gantry N at the same time.

The plug connection is simple, fast, and reliable. As an example, the first positioning members 201 are insertion holes and the second positioning members 202 are insertion blocks. However, the first positioning members 201 may also be insertion blocks and the second positioning members 202 may also be insertion holes.

As an example, the insertion block may be a pin and the insertion hole may be a pin hole.

Generally, the structure of the insertion block matches with the insertion hole. For example, when the insertion hole is a circular hole, the insertion block is a cylindrical block; and when the insertion hole is a diamond hole, the insertion block is a diamond column.

The outer contour of the insertion block may exactly match with the inner contour of the insertion hole to achieve an effect of stably positioning. The outer contour size of the insertion block may also be smaller than the inner contour size of the insertion hole. For example, the radial width of the insertion hole may be larger than that of the insertion block. In this case, the mounting mechanism according to this embodiment further includes an adjusting member, wherein the adjusting member 203 is movably mounted in the first positioning member 201 (i.e., the insertion hole), and the adjusting member is provided with a mounting hole matching with the second positioning member 202.

By setting the radial width of the first positioning member 201 (insertion hole) larger than that of the second positioning member 202 (insertion block) and making the adjusting member be movable in the insertion hole, the position of the treatment head on the gantry may be further adjusted appropriately to ensure a higher mounting accuracy. By forming the mounting hole fitting with the insertion block on the adjusting member, the first positioning member 201 and the second positioning member 202 are secured relative to each other.

The adjusting member includes an adjusting body, wherein the adjusting body is movably disposed inside the first positioning member 201; and a fixing body, wherein the fixing body is connected to an end portion of the adjusting body. The adjusting body is provided with the mounting hole, and the fixing body is configured to secure the adjusting body into the first positioning member 201 (insertion hole).

The position of the treatment head on the gantry can be finally adjusted by moving the adjusting body in the insertion hole. Upon determining the above positional relationship, the adjusting member is fixed relative to the insertion hole by the fixing body, thereby ensuring that the treatment head is fixed relative to the gantry.

For example, the fixing body may be in a plate-shaped structure surrounding the end portion of the adjusting body. At this time, the fixing body may be secured to the top support by screws, so as to fix the adjusting member relative to the insertion hole.

From the above, it can be known that the two lateral supports 1 may be separated and relatively independent. For simplification of the structure of the mounting mechanism and improving its strength, as shown in FIG. 1, the mounting mechanism further includes a reinforcing support 5, wherein two ends of the reinforcing support 5 are respectively connected to the two lateral supports 1.

For example, the reinforcing support 5 may be in a link structure, and there may be one or two reinforcing supports 5, wherein two ends of the reinforcing support 5 are respectively connected to the same side ends of the two lateral supports 1.

Further, the length of the reinforcing support 5 may be adjusted, such that the mounting mechanism may adapt to treatment heads M of various specifications.

As mentioned above, after the treatment head M is accurately disposed relative to the gantry N, the only requirement is to fasten and connect the treatment head M to the gantry N. Generally, the guide rail of the treatment head M and the mounting lateral plate P of the gantry N are connected by connecting screws. In view of that in practice, the lateral support 1 is clamped between the guide rail and the mounting lateral plate P, as shown in FIG. 4, the lateral support 1 and the positioning support 3 are provided with a via hole 6 to allow the connecting screws of the mounting lateral plate P and the guide rail to run, which is of great importance for improving the fastening performance.

Further, the length of via hole 6 may be set to be a certain value, and the length direction may be in an axial direction of the lateral support 1. For example, the via hole 6 may be a waist-shaped hole, which not only facilitates using a plurality of connecting screws at the same time, but also can improve the convenience of fastening connection.

According to another aspect of the embodiments of the present disclosure, a radiotherapy device is further provided. The radiotherapy device includes: any one of the mounting mechanisms according to the embodiments of the present disclosure; a treatment head, wherein a guide rail of the treatment head is connected to a lateral support of the mounting mechanism; and a gantry, wherein a mounting lateral plate of the gantry is connected to a positioning support of the mounting mechanism.

In view of the radiotherapy device, the following describes mounting and dismounting processes of the treatment head.

Mounting Process of Treatment Head:

First, a first fixing block of a positioning support of the mounting mechanism is connected to a mounting lateral plate of a gantry, and two lateral supports of the mounting mechanism are connected to guide rails on two sides of a treatment head. Then an entirety of the mounting mechanism and the treatment head are preliminarily mounted to the gantry. Specifically, a top support is connected to the top of the mounting lateral plate of the gantry under positioning actions of a first positioning member and a second positioning member, thus achieving accurate positioning and preliminary mounting of the treatment head on the gantry.

A first driving member may be configured to drive a first thickness adjusting block to move, such that the thickness of the positioning support may be increased until a mounting gap between the lateral support and the mounting lateral plate of the gantry is eliminated (i.e., the first thickness adjusting block is wedged tightly with the lateral support), and the positioning support is configured to provide lateral support for the treatment head, such that the treatment head may be fixed relative to the gantry. Then, connecting screws are used to fasten and connect the guide rail of the treatment head to the mounting lateral plate of the gantry. In the above mounting process, a high mounting accuracy may be acquired, and multiple radiation sources on the treatment head can always focus on an isocenter.

Dismounting Process of Treatment Head:

A gantry bracket is rotated to drive the gantry to rotate, so as to dispose the treatment head on one side of the gantry (i.e., the axis of the treatment head extends in a horizontal direction). The preliminary mounting of the treatment head on the gantry can be relieved.

The first driving member can be used to drive the first thickness adjusting block to move in an opposite direction, such that the thickness of the positioning support can be reduced until a gap between the lateral support and the mounting lateral plate of the gantry is regained (i.e., the first thickness adjusting block is separated from the lateral support), which facilitates the disassembly. Then, the thickness of an unloading support between the mounting lateral plate of the gantry and the guide rail of the treatment head is adjusted. Specifically, a second thickness adjusting block is driven to slide along a second fixing block by a second driving member to increase the thickness of the unloading support, so as to eliminate the gap between the lateral support and the mounting lateral plate of the gantry (i.e., the second thickness adjusting block is wedged tightly with the lateral support). The unloading support is configured to provide lateral support for the treatment head, such that the treatment head is favorably positioned relative to the gantry (this process can be understood as switching the positioning support to the unloading support). Since the unloading support is provided with a rolling member, which is configured to form rolling friction with the lateral support, based on the rolling friction, the treatment head may be successfully pulled out of the gantry by a treatment head dismounting tool (it should be understood that the treatment head may be pulled out of the gantry together with the lateral support and the top support of the mounting mechanism) after the fastening connection between the treatment head and the gantry is relieved. During remounting of the treatment head, the mounting accuracy of the remounted treatment head may be ensured only by returning along the original way and switching the unloading support to the lateral support.

The treatment head dismounting tool and the operation processes of dismounting and mounting the treatment head are common in the art, which are explained by examples.

A base of the treatment head dismounting tool is secured to a foundation on one side of the gantry, and is reliably connected to the foundation by screws. The treatment head dismounting tool can linearly move in three orthogonal directions to adjust postures of the treatment head. The treatment head dismounting tool is connected to the gantry to keep the balance of the gantry in the dismounting process. A horizontal guide rail on the treatment head dismounting tool may extend below the guide rail of the treatment head inside the gantry.

In the dismounting process, by adjusting the height of the treatment head dismounting tool, the upper and horizontal guide rail on the treatment head dismounting tool may be closely attached to the guide rail of the treatment head to lift the treatment head with the unloading support. A horizontal lead screw on the treatment head dismounting tool is secured to the guide rail of the treatment head by an adapter plate. The treatment head may be moved out of the gantry along the horizontal direction by hand-cranking the horizontal lead screw.

Described above are only for the purpose of helping those skilled in the art to understand the technical solutions of the present disclosure, but are not intended to limit the present disclosure. Within the spirit and principles of the present disclosure, any modifications, equivalent substitutions, improvements, and the like are within the protection scope of the present disclosure.

What is claimed is:

1. A mounting mechanism, comprising:
   two lateral supports respectively connected to two sides of a treatment head;
   top supports connected to tops of the lateral supports and configured to be connected to a top of a gantry; and
   positioning supports connected to the gantry and disposed between the lateral supports and the gantry, wherein thicknesses of the positioning supports are adjustable.

2. The mounting mechanism according to claim 1, wherein
   the positioning supports comprise a first fixing block connected to the gantry and a first thickness adjusting block slidable relative to the first fixing block; and
   the mounting mechanism further comprises a first driving member configured to drive the first thickness adjusting block to bidirectionally slide.

3. The mounting mechanism according to claim 2, wherein the first fixing block and the first thickness adjusting block are matched wedges.

4. The mounting mechanism according to claim 3, wherein the first driving member and the first thickness adjusting block are in threaded connection.

5. The mounting mechanism according to claim 1, further comprising unloading supports; wherein
   the unloading supports are connected to the gantry and disposed between the lateral supports and the gantry, and thicknesses of the unloading supports are adjustable; and
   the unloading supports are provided with rolling members, wherein the rolling members configured to form rolling friction with the lateral supports.

6. The mounting mechanism according to claim 5, wherein
   the unloading supports comprise a second fixing block connected to the gantry and a second thickness adjusting block slidable relative to the second fixing block; and
   the mounting mechanism further comprises a second driving member configured to drive the second thickness adjusting block to bidirectionally slide;
   wherein the rolling members are disposed on the second thickness adjusting block.

7. The mounting mechanism according to claim 6, wherein the second fixing block and the second thickness adjusting block are matched wedges.

8. The mounting mechanism according to claim 6, wherein the second driving member and the second thickness adjusting block are in threaded connection.

9. The mounting mechanism according to claim 6, wherein the rolling members comprise a fixed body fixed to the second thickness adjusting block and a plurality of balls rotatably disposed on the fixed body.

10. The mounting mechanism according to claim 1, further comprising:
    first positioning members disposed on the top supports; and
    second positioning members disposed at the top of the gantry;
    wherein the first positioning members and the second positioning members are in one-to-one correspondence.

11. A radiotherapy device, comprising: a mounting mechanism, a treatment head, and a gantry; wherein the mounting mechanism comprises: two lateral supports respectively connected to two sides of the treatment head; top supports connected to tops of the lateral supports and configured to be connected to a top of the gantry; and positioning supports connected to the gantry and disposed between the lateral supports and the gantry, wherein thicknesses of the positioning supports are adjustable;
    wherein the treatment head is connected to a lateral support of the mounting mechanism; and
    wherein the gantry is connected to a positioning support of the mounting mechanism.

12. The radiotherapy device according to claim 11, wherein the positioning supports comprise a first fixing block connected to the gantry and a first thickness adjusting block slidable relative to the first fixing block; and
    the mounting mechanism further comprises a first driving member configured to drive the first thickness adjusting block to bidirectionally slide.

13. The radiotherapy device according to claim 12, wherein the first fixing block and the first thickness adjusting block are matched wedges.

14. The radiotherapy device according to claim 13, wherein the first driving member and the first thickness adjusting block are in threaded connection.

15. The radiotherapy device according to claim 11, wherein the mounting mechanism further comprises unloading supports; wherein
    the unloading supports are connected to the gantry and disposed between the lateral supports and the gantry, and thicknesses of the unloading supports are adjustable; and
    the unloading supports are provided with rolling members, wherein the rolling members are configured to form rolling friction with the lateral supports.

16. The radiotherapy device according to claim 15, wherein the unloading supports comprise a second fixing block connected to the gantry and a second thickness adjusting block slidable relative to the second fixing block; and the mounting mechanism further comprises a second driving member configured to drive the second thickness adjusting block to bidirectionally slide;

wherein the rolling members are disposed on the second thickness adjusting block.

17. The radiotherapy device according to claim 16, wherein the second fixing block and the second thickness adjusting block are matched wedges.

18. The radiotherapy device according to claim 16, wherein the second driving member and the second thickness adjusting block are in threaded connection.

19. The radiotherapy device according to claim 16, wherein the rolling members comprise a fixed body fixed to the second thickness adjusting block and a plurality of balls rotatably disposed on the fixed body.

20. The radiotherapy device according to claim 11, wherein the mounting mechanism further comprises:

first positioning members disposed on the top supports; and second positioning members disposed at the top of the gantry;

wherein the first positioning members and the second positioning members are in one-to-one correspondence.

* * * * *